(12) United States Patent
Pfeiffer

(10) Patent No.: US 7,865,261 B2
(45) Date of Patent: Jan. 4, 2011

(54) METHOD AND DEVICE FOR PRODUCING DENTAL PROSTHESIS ELEMENTS

(75) Inventor: Joachim Pfeiffer, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 395 days.

(21) Appl. No.: 11/988,803

(22) PCT Filed: Jul. 17, 2006

(86) PCT No.: PCT/EP2006/064303

§ 371 (c)(1),
(2), (4) Date: Jan. 15, 2008

(87) PCT Pub. No.: WO2007/009964

PCT Pub. Date: Jan. 25, 2007

(65) Prior Publication Data

US 2009/0081616 A1    Mar. 26, 2009

(30) Foreign Application Priority Data

Jul. 15, 2005   (DE) .................. 10 2005 033 738

(51) Int. Cl.
*G06F 19/00* (2006.01)
*G03B 21/60* (2006.01)
*G06K 9/00* (2006.01)
*A61B 6/14* (2006.01)
*A63B 57/00* (2006.01)

(52) U.S. Cl. .................. 700/118; 700/95; 700/97; 700/98; 700/163; 359/458; 382/128; 382/154; 378/38; 378/39; 378/40; 473/201.1; 473/202.1

(58) Field of Classification Search .................. 700/95, 700/97–98, 118, 163; 359/458; 382/128, 382/154; 378/38–40; 473/201.1, 202.1

See application file for complete search history.

(56) References Cited

U.S. PATENT DOCUMENTS

| 4,575,805 | A | * | 3/1986 | Moermann et al. .......... 700/163 |
| 4,582,998 | A | * | 4/1986 | Gonser et al. ............ 250/492.1 |
| 4,837,732 | A | * | 6/1989 | Brandestini et al. ........... 433/29 |
| 5,372,502 | A | * | 12/1994 | Massen et al. .............. 433/215 |

(Continued)

FOREIGN PATENT DOCUMENTS

DE    19714526    10/1998

(Continued)

OTHER PUBLICATIONS

English Abstract of DE 19714526.

(Continued)

*Primary Examiner*—Ramesh B Patel
(74) *Attorney, Agent, or Firm*—Dykema Gossett PLLC

(57) ABSTRACT

A method for producing a dental prosthesis element wherein construction relating to the dental prosthesis element is recorded together with measurement data relating to the dental prosthesis element and is reproduced on a display, the measurement data having been recorded by a three-dimensional measurement device. A 3D data record of the tooth situation can be reproduced on the display instead of the construction data. A device for the partial manual treatment of the dental prosthesis element includes a three-dimensional measurement device, a display, and a computer unit for the correlation and comparison of two data records and for graphically presenting the data generated by the comparison.

26 Claims, 3 Drawing Sheets

U.S. PATENT DOCUMENTS

| | | | |
|---|---|---|---|
| 5,452,219 A * | 9/1995 | Dehoff et al. | 700/163 |
| 6,174,168 B1 * | 1/2001 | Dehoff et al. | 433/202.1 |
| 6,364,660 B1 * | 4/2002 | Durbin et al. | 433/29 |
| 6,648,640 B2 * | 11/2003 | Rubbert et al. | 433/24 |
| 6,885,464 B1 * | 4/2005 | Pfeiffer et al. | 356/602 |
| 2003/0003420 A1 | 1/2003 | Striezel | |
| 2004/0143351 A1 | 7/2004 | Rathke et al. | |
| 2004/0185422 A1 | 9/2004 | Orth et al. | |
| 2005/0060868 A1 | 3/2005 | McMurtry | |
| 2005/0070782 A1 | 3/2005 | Brodkin | |
| 2006/0008774 A1 * | 1/2006 | Orth et al. | 433/202.1 |
| 2006/0008776 A1 * | 1/2006 | Orth et al. | 433/215 |
| 2006/0199154 A1 | 9/2006 | Kraemer et al. | |

FOREIGN PATENT DOCUMENTS

| | | |
|---|---|---|
| DE | 19828003 | 1/2000 |
| DE | 10310751 | 7/2004 |

OTHER PUBLICATIONS

English Abstract of DE 10310751.
English Abstract of DE 19828003.

* cited by examiner

METHOD AND DEVICE FOR PRODUCING DENTAL PROSTHESIS ELEMENTS

BACKGROUND OF THE INVENTION

1. Field of the Invention

The invention relates to a method for the production of a dental prosthetic item, in which method the dental prosthetic item is machined manually.

The invention further relates to a method for the production of a dental prosthetic item comprising a framework and a superstructure.

Furthermore, the invention relates to devices for partial manual machining of a dental prosthetic item.

2. Prior Art

Methods are known in the prior art, in which dental prosthetic items are produced using computer-aided design and production techniques to various extents.

The older prior methods dispense entirely with the use of computers. In most cases, an impression of the dental situation is made both of the jaw that requires treatment and of the opposing jaw. This impression is used as the basis for the production of a positive model, on which a dental technician will produce the dental prosthetic items in several layers. Initially, a high-strength framework is produced, to which a plurality of porcelain or ceramic layers are then applied. The occlusion is examined using an articulator so that the dental prosthetic item fits in the patient's mouth in the best possible way.

The disadvantages of these methods are that, firstly, the contact surfaces are at most as precise as the situation model, which lacks proper dimensional accuracy due to the fact that an impression is made and the resulting model dries out. Secondly, the occlusion can be examined only with the aid of a mechanical articulator, so that flawless functional efficiency of the dental prosthetic item will greatly depend on the skill of the dental technician.

Furthermore, methods are known which no longer require the participation of a dental technician. The dental situation is scanned in the patient's mouth or on an impression by a 3D scanning device. Such scanning is usually performed optically. The scanned data then form the basis for creating a computer-aided design of the dental prosthetic item, which is then fabricated using computer-aided production techniques. Material removing processes, which machine the blanks, either exhibiting or lacking final strength properties, by computer-aided milling and grinding devices, are examples of production processes known in the prior art. Blanks that do not exhibit final strength are brought to their final strength by sintering or infiltration. In addition, it is known that dental prosthetic items can be produced by laser sintering or 3D printing.

The disadvantage of fully automatic production methods is that the dental prosthetic items only partially meet the aesthetic requirements, since a natural tooth has complex optical properties resulting from its multi-layered structure. These properties can be reproduced only to a certain extent when using a single-layered ceramics structure.

Furthermore, methods are known which combine manual production of dental prosthetic items with the automatic production of parts of the dental prosthetic item.

DE 101 31 131 A1 discloses a method for the production of a dental prosthetic item comprising individual teeth or groups of teeth, in which intraoral spatial information on the tooth stump or implant holding the prosthetic item is produced, and a model of the jaw or jaw section is prepared with the help of this information. Furthermore, CAD/CAM methods are used to produce a framework, which is adapted to match the dental situation and to which a dental technician manually applies a veneer made of ceramics material.

The disadvantage of the method described above is that the preparation of a model based on digital data is highly elaborate.

It is therefore an object of the present invention to specify methods and devices for the production of dental prosthetic items, enabling economical, accurate, and aesthetically immaculate production of a dental prosthetic item.

SUMMARY OF THE INVENTION

In the method of the invention for the production of a dental prosthetic item involving manual machining of the dental prosthetic item the design data of the dental prosthetic item to be manufactured are provided and following a machining step for the production of the dental prosthetic item a 3D scanning device provides scanned data of the machined dental prosthetic item to be produced and the data are displayed on a monitor together with the design data.

The advantage of this method is that the dental technician on the one hand retains complete aesthetic control of the production of the dental prosthetic item and, on the other hand, has the assurance, by effecting comparison with a digital design, of producing an accurately fitting, high-quality dental prosthetic item in an economical manner. Moreover, he does not require any more models of the dental situation other than the design data.

The method is suitable for manufacturing all types of dental prosthetic items, for example, crowns, bridges, veneers, implants, and the like, and is particularly advantageous for the production of dental prosthetic items having a surface which is visible when the patient's mouth is open and which is therefore subject to high aesthetic demands.

Advantageously, a correlation between the scanned data and the design data is established and the differences between the scanned data and the design data are displayed on the monitor. This facilitates comparison with the design data.

Advantageously, when designing the dental prosthetic item, contact points or surfaces, particularly an inner surface, are provided to enable the dental prosthetic items to be accurately positioned in a holding device of a scanning device. Said holding device preferably has a contact surface, which is adapted to match the inner surface of the dental prosthetic items. This enables scanning of the dental prosthetic items to take place from constantly the same position, which is determined by the position of the contact points or surfaces. The inner surface is particularly suitable for this purpose.

Advantageously, at least one reference surface is provided on the holding device or on the dental prosthetic item. The relative position of the reference surface to the contact points or surfaces of the dental prosthetic item is known. Correlation between the scanned data and the design data is established by way of the reference surface. It is thus possible to accurately determine the position of the dental prosthetic item following mounting thereof in the patient's mouth, since non-uniform layer thicknesses, if present, can result in inaccuracies.

Correlation between the 3D data set of the dental situation, the design data, and the scanned data is advantageously established, and these data are displayed on the monitor. The dental technician is thus able to control the effect of the dental prosthetic item in its subsequent environment and to adapt the design data accordingly, in an advantageous refinement of the invention.

In particular, it is advantageous if the 3D data set of the dental situation also includes the opposing jaw. It is possible to move the two jaw halves relatively to each other by a software articulator started and running on a computer. The dental technician thus has the option of examining both the static and the dynamic occlusion of the dental prosthetic item, in particular, if the software articulator is advantageously equipped with a collision monitor, which displays the contact points of both jaw halves.

The 3D data set of the dental situation is advantageously produced by three-dimensional intraoral scanning or three-dimensional scanning of an impression or a model.

The 3D data set of the dental situation and/or the design data are advantageously provided by remote transmission. This reduces the production time.

The dental prosthetic item is advantageously composed of a plurality of parts. One of the parts represents a framework, which is designed and produced by CAD/CAM methods. The presence of a physical model of the dental situation is thus unnecessary, since the contact surfaces of the dental prosthetic item are directly known from the scanned data. The framework will therefore exhibit excellent fitting accuracy.

At least one inner surface of the framework is advantageously designed as a contact point or surface. The holding device has a contact surface that mates with this inner surface. It is thus possible to accurately position the framework in the holding device.

Another aspect of the invention relates to a method for the production of a dental prosthetic item, comprising a framework and a superstructure. A 3D data set of a dental situation of a patient is provided and scanned data of the framework or the dental prosthetic item mounted at least partially thereon are acquired. The scanned data and the 3D data set of the dental situation are displayed on a monitor. The dental technician can thus examine the dental prosthetic item in its subsequent clinical environment.

The framework is advantageously designed and produced by CAD/CAM methods based on the 3D data set of the dental situation. This enables particularly rapid and accurate production of the framework and reduces the expenditure of time, costs, and effort.

Advantageously, a correlation between the scanned data and the 3D data set of the dental situation in correct size and position is established. It is thus possible to effectively observe the effect of the dental prosthetic item in its clinical environment.

This can be accomplished particularly easily when the correlation is displayed graphically.

Contact points or surfaces are advantageously provided when designing the framework. These contact points or surfaces enable accurate positioning of the framework on a holding device of the scanning device. This enables the dental prosthetic item to be measured from exactly the same position each time.

Advantageously, at least one reference surface is provided on the holding device or on the dental prosthetic item or on the framework. The relative position of the reference surface to the contact points or surfaces of the framework is known. A correlation between the scanned data and the data set of the dental situation is established by way of the reference surface. This enables the position of the contact surfaces to be determined accurately with respect to the outer contour of the dental prosthetic item.

Another aspect of the invention relates to a device for partial manual machining of a dental prosthetic item. The device comprises a 3D scanning device for the production of scanned data of the dental prosthetic item to be produced and a computer, and a monitor. The computer comprises a first memory for storing a first three-dimensional data set and a second memory for storing the scanned data. The computer is connected to the monitor for displaying the two data sets. The computer can correlate and compare the two data sets and convert the data acquired by said comparison for graphic display. Such a device makes it possible to produce a dental prosthetic item with the precision of computer-aided production methods and with the aesthetic properties of hand-made dental prosthetic items.

The device advantageously comprises a computer-aided production unit for the production of a part of the dental prosthetic item. In particular, that hidden part of the dental prosthetic item that represents the contact surfaces of the preparation site in the patient's mouth can be produced on the basis of the digital data, with high precision.

The first 3D data set is advantageously a 3D data set of the dental situation in the patient's mouth. The effect of the dental prosthetic item in the patient's mouth can then be estimated on the monitor.

Alternatively, the first 3D data set can comprise design data of the dental prosthetic item to be produced. The scanned dental prosthetic item and the design data can then be compared, thereby effectively ensuring dimensional accuracy of the dental prosthetic item.

The computer advantageously comprises a third memory for storing design data together with the 3D data of the dental situation. All three data sets are displayed on the monitor. This provides a particularly lucid and graphical representation.

The data set of the dental situation advantageously also includes the opposing jaw. A stored software articulator for computing the relative movement of the two jaws can be started on the computer and be graphically displayed on the monitor. This makes it possible for the dental technician to examine both the static and the dynamic occlusion. This is accomplished particularly advantageously when the software articulator comprises a collision monitor, which displays the contact points between the two jaws.

Advantageously, a holding device is provided on which the dental prosthetic item can be mounted in a fixed position. The holding device comprises one or more reference surfaces for determining the shape and position of the dental prosthetic item in relation to its contact points or surfaces. The contact points or surfaces are not visible on the scan and their position in relation to the outer surfaces cannot be determined accurately due to the material applied.

It is particularly advantageous when the holding device comprises contact surfaces that mate with the contact surfaces of the dental prosthetic item. This ensures very correct positioning of the dental prosthetic item on the holding device.

A final aspect of the invention relates to a device for partial manual machining of a dental prosthetic item. This device comprises a 3D scanning device for the production of scanned data of the dental prosthetic item to be machined, a computer, and a monitor. The computer comprises a first memory for storing a first three-dimensional data set and a second memory for storing scanned data. The computer is connected to the monitor for displaying the two data sets. Furthermore, a holding device is provided, on which the dental prosthetic item can be mounted in a fixed position. The holding device has one or more reference surfaces for determining the shape and position of the dental prosthetic item with respect to its contact points or surfaces. Such a device enables partial manual production of a dental prosthetic item in a very easy manner.

The holding device advantageously includes a cast of the inner surface of the dental prosthetic item, which cast is made of a hardenable material, preferably gypsum. It is thus very easy to produce a holding device that is very suitable for producing the individual dental prosthetic item.

The device advantageously comprises a computer-aided production unit for the production of a framework. It is thus possible to accurately produce the framework with the contact surfaces relating to the preparation site in the patient's mouth. This ensures good functionality of the dental prosthetic item.

The first 3D data set is advantageously a 3D data set of the dental situation in the patient's mouth. The scanned data can thus be displayed on the monitor together with the 3D data set of the dental situation.

Alternatively, the first 3D data set can consist of design data of the dental prosthetic item to be produced. This makes it possible for the dental technician to compare the dental prosthetic item with the design input.

The computer advantageously comprises a third memory for storing design data of the dental prosthetic item in addition to the 3D data set of the dental situation in the patient's mouth. All three data sets are displayed on the monitor. This provides the possibility of very good monitoring of the dental prosthetic item.

It is particularly advantageous when the data set of the dental situation also includes the opposing jaw. A stored software articulator for computing the relative movement of the two jaws can be started on the computer and graphically displayed on the monitor. It is thus possible to check both the static and the dynamic occlusion.

Furthermore, another advantage of the device is that the dental technician no longer requires physical impressions of the dental situation. These impressions are frequently inaccurate, since they widen when being removed from the patient's mouth and then change their size during the drying process. The expected fitting accuracy is less than or at most equal to that achieved in a high-precision intraoral three-dimensional scan.

BRIEF DESCRIPTION OF THE DRAWINGS

The method of the invention is explained below with reference to the drawings, in which.

DESCRIPTION OF AN EMBODIMENT

Figure 1:
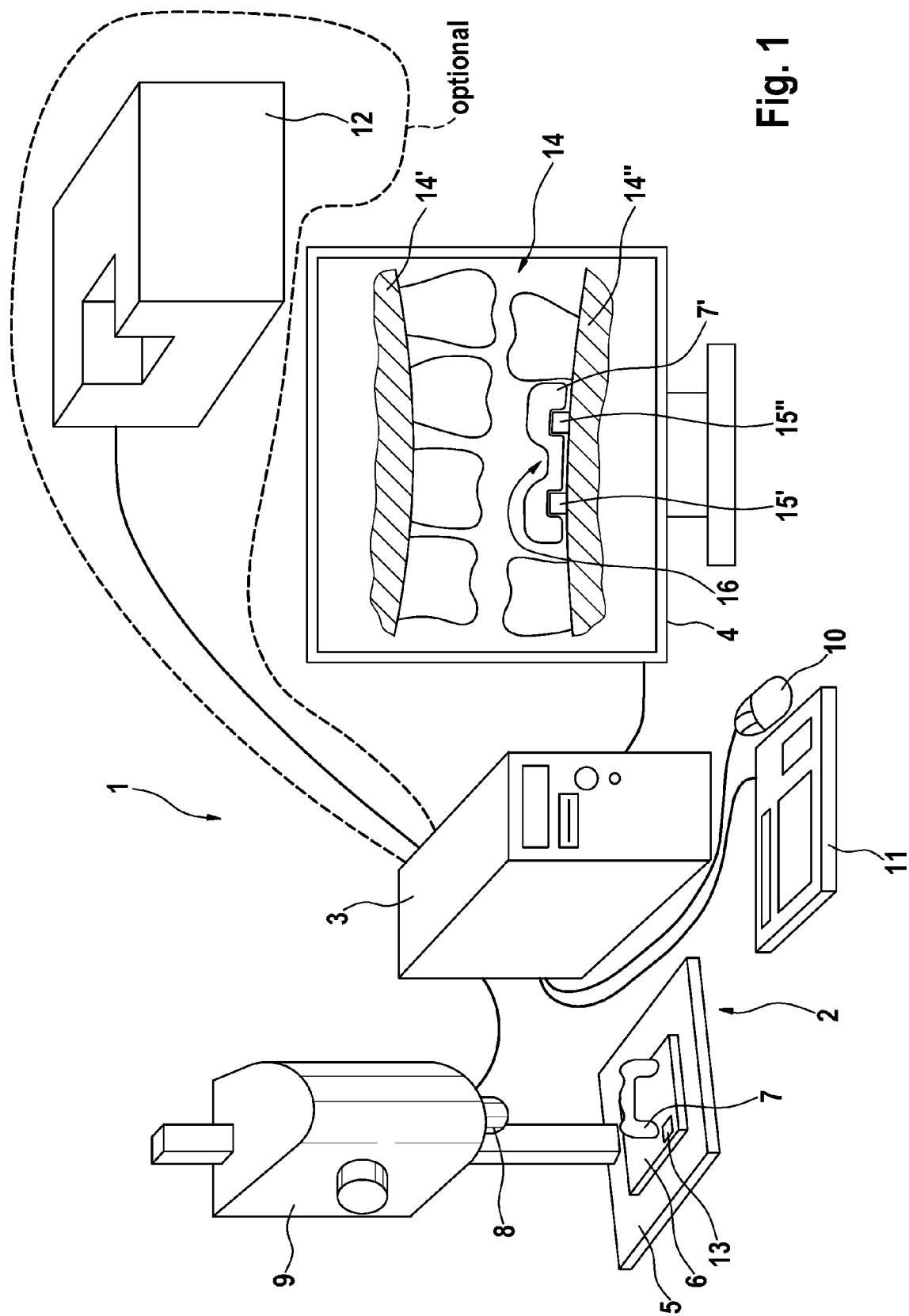
FIG. 1 is a view of the device of the invention for the production of a dental prosthetic item.

FIG. 1 shows a device 1 used for the partial manual production of a dental prosthetic item 7. The device 1 substantially comprises a 3D scanning device 2, a computer 3, and a monitor 4.

A holding device 6 holding a dental prosthetic item 7, which is accurately positioned thereon and which requires finishing, is located on the base plate 5 of the 3D scanning device 2. The dental prosthetic item 7 is positioned by the holding device 6 in the field of view of scanning optics 8 of the three-dimension scanning device 2. The scanning optics 8 are accommodated in a vertically adjustable housing 9 of the 3D scanning device 2 and are preferably designed to be telecentric.

The 3D scanning device 2 is connected to the computer 3, which is inputted via a mouse 10 and a keyboard 11. The computer 3 itself is connected to the monitor 4.

Optionally, the computer 3 can be connected to a grinding machine 12 adapted to effect computer-aided machining of parts of the dental prosthetic item 7. Especially the high-strength framework of the dental prosthetic item 7 to be attached via its contact surfaces to the prepared tooth or teeth of the patient can be produced using the grinding machine 12, since CAM methods are not only very precise but also dispense with the use of a physical model of the dental situation, for example, in the form of an impression.

The design data required for producing the dental prosthetic item 7 and produced by means of CAD methods based on scanned data of the dental situation can be compiled and transmitted by the dentist or they can be produced by the dental technician himself with the aid of the computer 3.

Figure 4A:
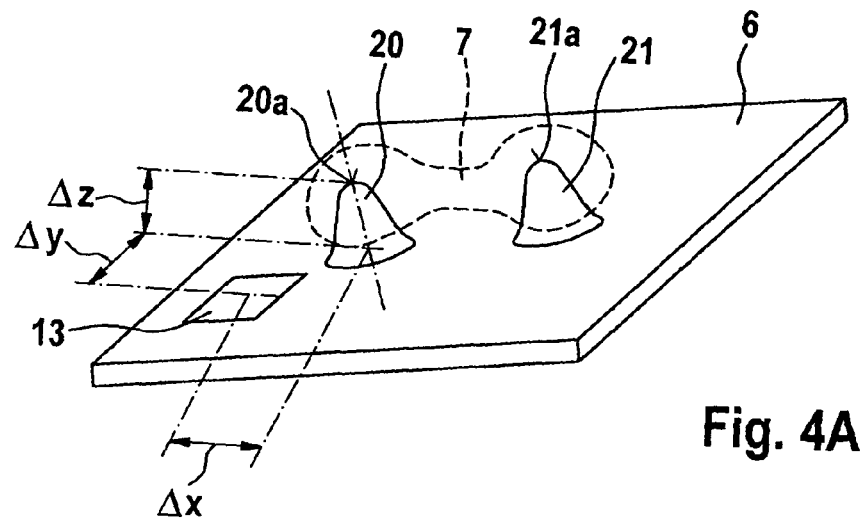
FIGS. 4A and 4B are views of a holding device comprising reference surfaces.
Figure 4B:
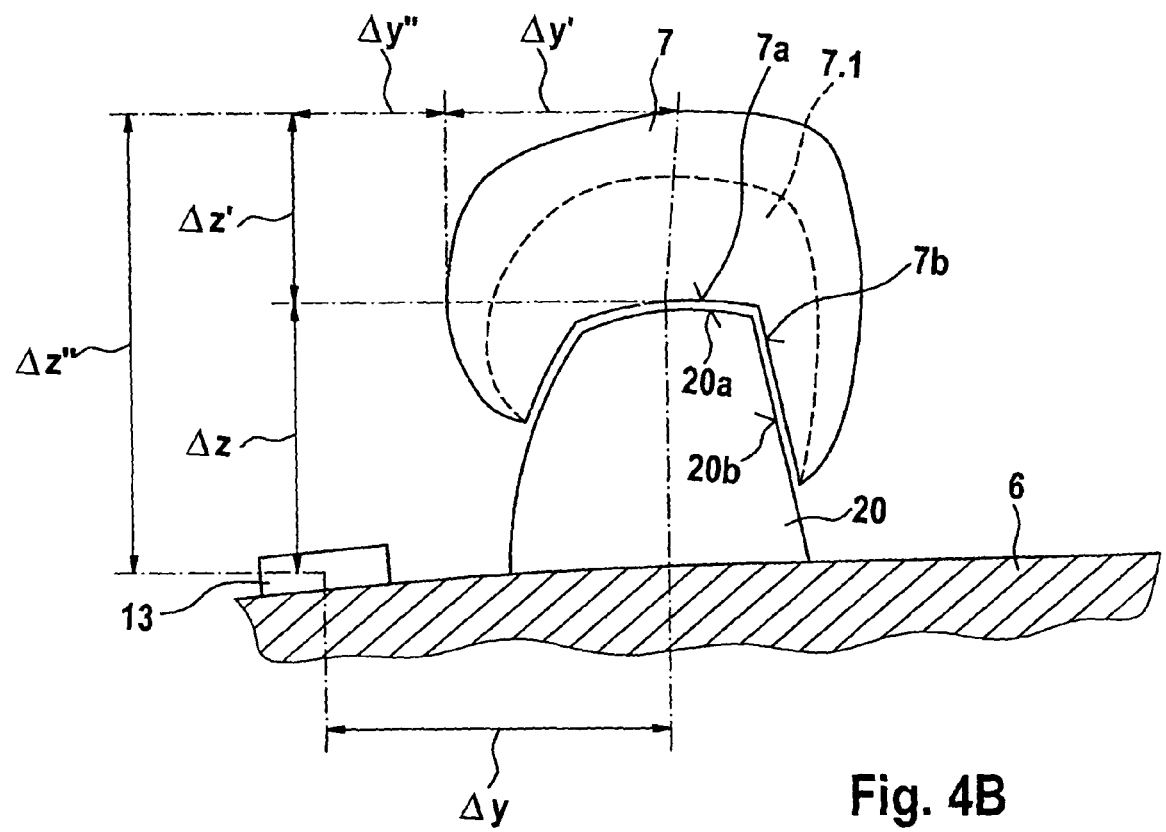

For the framework 7.1 produced by the grinding machine 12, a holding device 6 is first prepared, as described in more detail in FIGS. 4A and 4B. The dental technician then manually veneers the framework 7.1, which thus obtains excellent aesthetic properties in addition to a very good accuracy of fit.

The procedure of finishing the dental prosthetic item 7 on the framework 7.1 as base is described below.

In a first step, the 3D scanning device 2 is used to scan the framework 7.1 and a reference surface 13 attached to the holding device 6. The significance of the reference surface 13 is explained in more detail in FIGS. 4A and 4B. The scanned data are transmitted to the computer 3 and evaluated by the same.

In order to finish the dental prosthetic items 7 by veneering the framework 7.1 by the slip-casting method, the dental technician applies a slip layer to the unfinished dental prosthetic item 7. For this purpose, he can remove the dental prosthetic item 7 from the holding device 6 and machine it in his preferred working position. After application and modeling of the slip layer, the dental prosthetic item 7 is accurately replaced on the holding device 6 and positioned on the base plate 5 of the 3D scanning device 2. Another scan is then started.

Further scanning of the dental prosthetic item 7 can alternatively be performed offset from the previous scan in relation to the scanning device 9, if the dimensions of the dental prosthetic item 7 are larger than the imaging range of the scanning optics 8. Rotated scanning about a horizontal axis is also possible, if it is necessary to make the undercuts visible, which are otherwise not visible to the view of the scanning optics system 8.

A graphical evaluation unit forming part of the computer 3 processes the scanned data and any additional three-dimensional data sets and presents them to the monitor 4. The current shape 7' of the dental prosthetic item 7 is then displayed to the dental technician on the monitor 4. Thereupon, the dental technician can make corrections to the dental prosthetic item and rescan the corrected dental prosthetic item 7 until the prosthetic item 7 has acquired the desired shape. The display on the monitor 4 can be freely selected so that the dental technician can examine the representation 7' of the dental prosthetic item 7 from all sides. The slip layer is then baked. The dental technician repeats the steps described above—application of slip layer, modeling of slip layer, scanning the dental prosthetic item, correcting the dental prosthetic item, scanning the corrected dental prosthetic item, baking the slip layer—until the dental prosthetic item is finished to completion.

As a final step, the production process is documented.

The computer 3 supports the dental technician in a number of ways:

Software suitable for producing 3D images from 3D data sets is started on the computer 3. A plurality of 3D data sets can be correlated with each other matching in position and orientation. A joint 3D data set can be produced therefrom, which is displayed on the monitor 4.

A data set 7' is formed on the basis of the last scan of the dental prosthetic item 7 using the 3D scanning device 2. In a first variant, a correlation between this data set 7' and the 3D data set of the dental situation 14 is established and an image is produced therefrom, which is displayed on the monitor 4. The image 7' of the dental prosthetic item 7 is correctly inserted into the dental situation 14 of the patient's mouth. The dental prosthetic item 7 is here in the form of a bridge resting on two pillars 15', 15".

This display provides the dental technician with the possibility of examining the dental prosthetic item 7 in its subsequent environment and of performing an adaptation, for example, of its height and its width in the mesial, distal, buccal, and lingual directions in order to achieve a uniform appearance and good functionality of the dental prosthetic item.

A software articulator is started on computer 3. This software articulator makes it possible to move the opposing jaw 14' relatively to the jaw 14". The points of contact between the teeth of the jaw 14" and those of the opposing jaw 14' are determined by a collision monitor and are displayed on the monitor.

Figure 2:
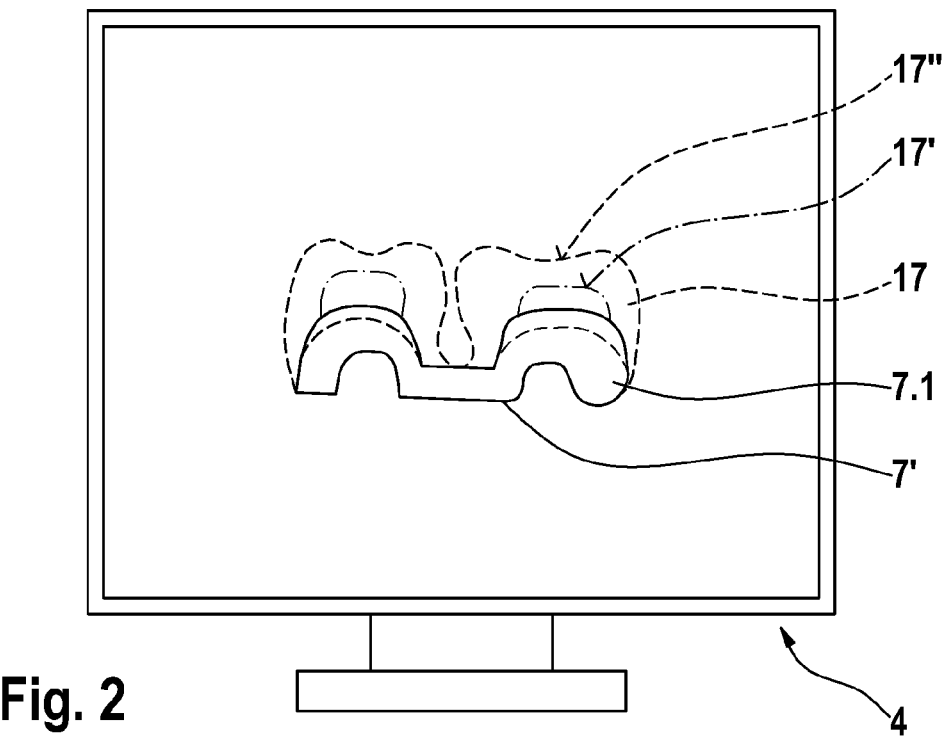
FIG. 2 illustrates a first method for displaying the dental prosthetic item on a monitor.

FIG. 2 shows another display option. If a 3D data set of the design of the dental prosthetic item to be completed is available, the computer 3 can establish a correlation between the design data (17, 17', 17") and the scanned data (7') of the dental prosthetic item 7. The dental prosthetic item 7 to be fabricated is represented in a multi-layered, transparent form, the layer boundaries 17' and 17" indicating the use of different materials for producing the dental prosthetic item 7. The image 7' of the unfinished dental prosthetic item 7 is inserted into the transparent, three-dimensional representation of the design data in the correct position such that the dental technician will recognize differences between the existing physical dental prosthetic items 7 and the design data set. He then has the option of applying or removing material at the incorrectly fitting locations and can re-scan the dental prosthetic item 7 until the dental prosthetic item 7 and the design input are adequately in register.

Figure 3:
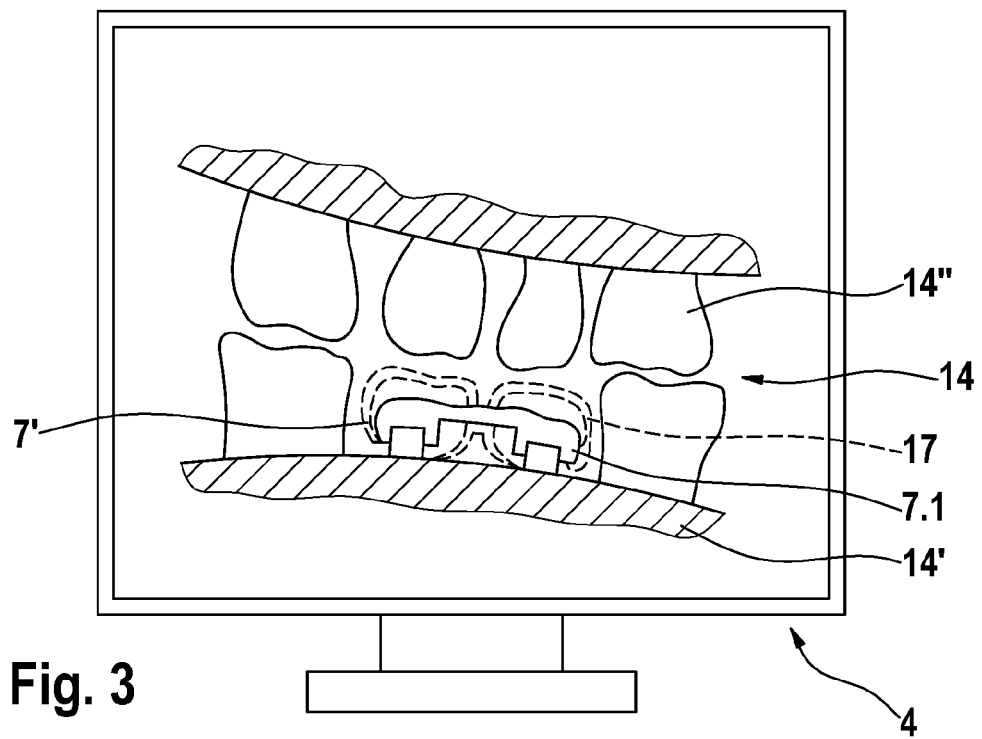
FIG. 3 illustrates a second method for displaying the dental prosthetic item on a monitor.

As shown in FIG. 3, it is possible to combine the image 7' of the dental prosthetic item 7 with the design data 17, 17', 17", and the 3D data set of the dental situation 14 in correct positions and to display the same on the monitor 4.

The position and size of the reference surface 13 are implemented for achieving correct positioning of the dental prosthetic item 7 in relation to the scanned data derived from the patient's mouth. FIG. 4A shows an enlarged view of the holding device 6. The reference surface 13 is attached to the holding device 6. The contour and size of the reference surface 13 is known to the computer. The holding device 6 comprises two raised portions 20, 21 resulting from casting the inner surfaces of the framework 22 (shown in dashed lines) of the dental prosthetic item 7 using gypsum. The raised portions 20, 21 thus form contact surfaces for the contact surfaces of the dental prosthetic items 7 on the prepared tooth stumps 15', 15". The raised portions 20, 21 can alternatively be produced by carving with the grinding machine 12.

For the purpose of establishing positionally correct correlation between the dental prosthetic item 7 and the dental situation 14 or the design data 17 using the computer 3, it is necessary to know the position of the contact surfaces of the dental prosthetic item 7, which contact the prepared tooth site, in relation to the outer contour of the dental prosthetic item 7. Since there no longer exists any fixed positional relationship on an already machined dental prosthetic item 7, it is necessary to execute external referencing.

In order to determine the positional relationship between the reference surface 13 and the raised portion 20, an image is made of the holding device 6 without the dental prosthetic item being fitted thereon. The relative position, given by the distance of the contact surface 20a ($\Delta x$, $\Delta y$, $\Delta z$) in the three spatial directions from the reference surface 13, is thus determined.

This procedure is also carried out for the other raised portion 21, with the help of which the position of the contact surface 21a of the raised portion 21 relative to the reference surface 13 is clearly determined.

Scanning the dental prosthetic item 7 fitted on the raised portions 20, 21, makes it possible to determine the position of the reference surface 13 and thus to conclude the position of the contact surfaces of the dental prosthetic item 7.

This is clearly visible in FIG. 4B. Those inner surfaces 7a and 7b of the dental prosthetic items 7 which are designed as contact surfaces fit the contact surfaces 20a and 20b of the raised portion 20. The distances $\Delta y$ and $\Delta z$ of the contact surface 20a and thus of the contact surface 7a are known to the system from the scan of the holding device 6 without the dental prosthetic item 7 fitted thereon. Scanning of the dental prosthetic item 7 and the reference surface 13 in a first step determines the distance between the reference surface 13 and the borders of the dental prosthetic item $\Delta z''$, $\Delta y''$. The distances $\Delta y'$ and the layer thickness $\Delta z'$ are then determined by computing the difference.

The holding device 6 makes it possible to remove the dental prosthetic items 7 for machining purposes and to quickly reattach it to the holding device in a defined position.

The invention claimed is:

1. A method for the production of a dental prosthetic item, in which the dental prosthetic item is manually machined, wherein design data of said dental prosthetic item to be fabricated are present, wherein the design of said dental prosthetic item includes an inner surface that ensures an unambiguous position of said dental prosthetic item in a holding device of a scanning system, and the holding device has a contact surface which matches said inner surface, and after a machining step for production of the dental prosthetic item, scanned data of the machined prosthetic item to be fabricated positioned in the holding device are recorded with a 3D scanning device and are displayed on a monitor together with design data.

2. The method according to claim 1, wherein a correlation between said scanned data and said design data is established and differences between said scanned data and said design data are indicated on the monitor.

3. The method according to claim 2, wherein at least one reference surface is provided on said holding device or on said dental prosthetic item, the position of said reference surface relative to said contact points or surfaces of said dental prosthetic item being known, and a correlation between said scanned data and said design data is established by way of said reference surfaces.

4. The method according to claim 1, wherein a correlation between 3D data set of a tooth situation, said design data, and said scanned data is established and these data are displayed on said monitor.

5. The method according to claim 4, wherein said 3D data set of the tooth situation includes the opposing jaw, and the two jaws can be moved relatively to each other by a software articulator loaded and running on a computer unit.

6. The method according to claim 4, wherein said 3D data set of said tooth situation is produced by three-dimensional intraoral scanning or three-dimensional scanning of an impression or model.

7. The method according to claim 4, wherein said 3D data set of said tooth situation and/or said design data are provided by remote transmission.

8. The method according to claim 1, wherein said dental prosthetic item is multipartite, and one of the parts is a framework designed and produced by CAD/CAM methods.

9. The method according to claim 8, wherein at least one inner surface of said framework is a contact point or a contact surface and said holding device has a contact surface that matches said inner surface.

10. A method for the production of a dental prosthetic item, in which said dental prosthetic item comprises a framework and a superstructure, wherein a 3D data set of a tooth situation of a patient is present and that a 3D scanning device is implemented to produce scanned data of said framework or of said dental prosthetic item at least partially formed thereon, wherein the design of said framework includes inner surfaces which enable unambiguous positioning of said framework in a holding device of the scanning device, and the scanned data and the 3D data set of the tooth situation are displayed on a monitor.

11. The method according to claim 10, wherein said framework is designed and produced by CAD/CAM methods on the basis of said 3D data set of the tooth situation.

12. The method according to claim 10, wherein a correlation between said scanned data and said 3D data set of said tooth situation matching in size and position is established.

13. The method according to claim 10, wherein the display on said monitor is graphical.

14. The method according to claim 10, wherein at least one reference surface is provided on said holding device or on said dental prosthetic item or on said framework, the position of said reference surface relative to said inner surfaces of said framework being known, and a correlation between the scanned data and the data set of the tooth situation is established by way of said reference surface.

15. A device for partial manual machining of a dental prosthetic item, comprising a 3D scanning system for the production of scanned data relating to the dental prosthetic item to be machined, and also a computer unit and a monitor, wherein the computer unit comprises a first memory for storing a first three-dimensional data net and a second memory for storing scanned data, and wherein the computer unit is connected to the monitor for displaying the two data sets and the computer unit correlates and compares the two data sets and also converts the data acquired by the comparison for graphical display, the device including a holding device on which said dental prosthetic item can be mounted in a fixed position, the holding device having one or more reference surfaces for determination of the shape and position of said dental prosthetic item with reference to inner surfaces thereof and wherein said holding device has contact surfaces which mate with said inner surface of said dental prosthetic item.

16. The device according to claim 15, wherein said device includes a computer-aided production unit for the production of a part of said dental prosthetic item.

17. The device according to claim 15, wherein a first 3D data set is a 3D data set of the tooth situation in the mouth of the patient.

18. The device according to claim 17, wherein said computer unit comprises a third memory area for storing design data of said dental prosthetic item to be fabricated, all three data sets being displayed on said monitor.

19. The device according to claim 17, wherein said data set of the tooth situation includes an opposing jaw and a software articulator for computing the relative movement of the two jaws is installed and runnable on said computer unit.

20. The device according to claim 15, wherein a first 3D data set consists of design data of said dental prosthetic item to be fabricated.

21. A device for partial manual machining of a dental prosthetic item, comprising a 3D scanning system for the production of scanned data relating to the dental prosthetic item to be machined, and also a computer unit, and a monitor, and the computer unit has a first memory area for the storage of a first three-dimensional (3D) data set and a second memory area for the storage of the scanned data, and the computer unit is connected to the monitor for displaying of the two data sets, and furthermore including a holding device on which said dental prosthetic item can be mounted in a fixed position, the holding device having one or more reference surfaces for determination of the shape and position of said dental prosthetic item with reference to inner surfaces thereof, and wherein said holding device includes a cast of the inner surface of said dental prosthetic item of a hardenable material.

22. The device according to claim 21, wherein said device includes a computer-aided production unit for the production of a framework.

23. The device according to claim 21, wherein the first 3D data set is a 3D data set of the tooth situation in the mouth of the patient.

24. The device according to claim 23, said computer unit has a third memory area for storage of design data of the dental prosthetic item to be fabricated, all three data sets being displayed on said monitor.

25. The device according to claim 23, said data set of the tooth situation includes an opposing jaw and a software articulator for computing the relative movement of the two jaws is installed and runnable on said computer unit.

26. The device according to claim 21, wherein the first 3D data set consists of design data of the dental prosthetic item to be fabricated.

* * * * *